United States Patent
Zhang

(10) Patent No.: US 9,952,180 B2
(45) Date of Patent: Apr. 24, 2018

(54) DELAMINATION SENSOR FOR ENGINE FAN BLADE

(71) Applicant: ROLLS-ROYCE plc, London (GB)

(72) Inventor: Bing Zhang, Derby (GB)

(73) Assignee: ROLLS-ROYCE plc, London (GB)

( * ) Notice: Subject to any disclaimer, the term of this patent is extended or adjusted under 35 U.S.C. 154(b) by 57 days.

(21) Appl. No.: 15/179,095

(22) Filed: Jun. 10, 2016

(65) Prior Publication Data
US 2017/0003252 A1    Jan. 5, 2017

(30) Foreign Application Priority Data
Jul. 3, 2015  (GB) .................................. 1511686.6

(51) Int. Cl.
*G01N 27/82* (2006.01)

(52) U.S. Cl.
CPC .................... *G01N 27/82* (2013.01)

(58) Field of Classification Search
CPC . G01M 5/0033; G01N 21/8806; G01N 27/82; G01N 27/902; G01N 27/9026; G01N 27/9033; G01N 27/904; G01R 15/181
USPC .................................................. 324/238, 243
See application file for complete search history.

(56) References Cited

U.S. PATENT DOCUMENTS

| | | | | |
|---|---|---|---|---|
| 5,028,100 A * | 7/1991 | Valleau | ............. | G01N 27/9046 324/232 |
| 5,453,291 A | 9/1995 | Sasahara et al. | | |
| 5,814,729 A * | 9/1998 | Wu | ...................... | G01M 5/0033 356/32 |
| 2013/0011625 A1 * | 1/2013 | Jevons | ..................... | F01D 5/282 428/172 |
| 2014/0023837 A1 | 1/2014 | Miller et al. | | |
| 2014/0327433 A1 * | 11/2014 | Anway | ................. | B29C 65/483 324/239 |
| 2015/0185128 A1 * | 7/2015 | Chang | ................. | G01M 5/0091 702/35 |

FOREIGN PATENT DOCUMENTS

FR    3 004 748 A1    10/2014

OTHER PUBLICATIONS

Ivana K. Partridge et al., Delamination resistant laminates by Z-Fiber pinning: Part I manufacture and fracture performance (Jun. 17, 2004) (available at sciencedirect.com; last accessed Sep. 20, 2017).*

Jan. 11, 2016 Search Report issued in British Patent Application No. 1511686.6.

* cited by examiner

*Primary Examiner* — Tung X Nguyen
*Assistant Examiner* — Robert P Alejnikov, Jr.
(74) *Attorney, Agent, or Firm* — Oliff PLC

(57) ABSTRACT

A composite component comprising a plurality of plies and a plurality of pins extending transversely to the plies, wherein the pins comprise a magnetic material. A magnetic field generator is configured to generate a magnetic field through a thickness direction of the component; and a sensor is provided for detecting a change in magnetic flux indicative of delamination of the plies.

18 Claims, 8 Drawing Sheets

DELAMINATION SENSOR FOR ENGINE FAN BLADE

TECHNICAL FIELD

The present disclosure concerns a composite component, a gas turbine engine, a method of manufacture of a composite component, and/or a method of detecting and/or resisting delamination of a composite component.

BACKGROUND

Gas turbine engines are typically employed to power aircraft. Typically a gas turbine engine will comprise an axial fan driven by an engine core. The engine core is generally made up of one or more turbines which drive respective compressors via coaxial shafts. The fan is usually driven off an additional lower pressure turbine in the engine core.

The fan comprises an array of radially extending fan blades mounted on a rotor. The fan blades and/or a casing that surrounds the fan may be manufactured from metallic and/or composite laminate materials. Generally fan blades include a composite body and may be provided with a metallic leading edge and/or a metallic trailing edge.

Composite components are often laminate structures that include a plurality of plies. Each ply generally includes reinforcing fibres (e.g. high strength or high stiffness fibres) embedded in a matrix, e.g. a plastic matrix material. The matrix material of adjacent stacked plies is bonded together to build the composite component. The matrix material is weaker than the fibre material and as such the bond between stacked plies can form a point of weakness. This means that a primary failure mechanism of concern for composite materials is delamination.

Delamination for example of a fan blade may occur in the event of an impact by a foreign object such as a bird strike.

To reduce the risk of delamination of a composite component through-thickness reinforcement can be used. One type of through-thickness reinforcement is pinning (which may also be referred to as Z-pinning). A component that has been pinned includes a plurality of pins (which may be referred to as Z-pins or rods) extending through the thickness of the component in a direction transverse to the general direction of the plies. The pins are generally made of a metallic or composite material and typically have a diameter ranging from or equal to approximately 0.3 mm to 0.5 mm. Often, composite pins are manufactured by pultrusion of a carbon fibre tow impregnated by a thermoset resin. The pins of a composite component exert a bridging force on the plies to hold the plies in position relative to each other, this suppresses opening of inter-laminar cracks (known as mode I failure) and sliding displacements of inter-laminar cracks (known as mode II failure).

Although the pins used in through-thickness reinforcement can substantially arrest crack propagation, it is often not possible to eliminate crack propagation in a composite component. Accordingly, it would be useful to detect when delamination has occurred, and the extent and/or location of such delamination so as to indicate when a component needs repair or replacement.

SUMMARY

In a first aspect there is provided a composite component comprising a plurality of plies and a plurality of pins extending transversely to the plies. The pins comprise a magnetic material. A magnetic field generator is configured to generate a magnetic field through a thickness direction of the component. A sensor is provided for detecting a change in magnetic flux. The change in magnetic flux is indicative of delamination of the plies.

When delamination occurs, often the pins start to deform and/or pull-out from the plies. This pull-out and/or deformation of the pins can cause a change in magnetic flux, this change in magnetic flux can be used to detect when delamination has occurred or deteriorated.

The composite component may comprise a sensor in regions where prevention of delamination is critical and no sensors may be provided in regions where delamination is acceptable.

The sensor may comprise an electrically conductive coil provided around one or more of the plurality of pins.

The coil may be provided on a surface of one or more of the plurality of plies. In exemplary embodiments, the coil may be provided on one or more outer surfaces of the composite component. For example, a coil may be provided on two opposing sides of the component, e.g. on surfaces of the component that define a principle plane of the laminates. In alternative embodiments, the coils may be provided on surfaces of the plies of the laminates that are not external to the laminate.

The coils may be made from any suitable conductive material. For example the coils may comprise a metal and/or a metal alloy.

The coil may be made from copper or an alloy thereof.

The magnetic field generator may comprise a coil through which electrical current can be directed.

The coil may comprise any suitable (electrically) conductive material. For example the coil may comprise a metal and/or a metal alloy. The coil may be made from copper or an alloy thereof.

In exemplary embodiments, the sensor may be one or more sensing coils and the magnetic field generator may be one or more excitation coils. In such embodiments, one of the excitation coils may be arranged to surround the one or more sensing coils. In alternative embodiments, one of the sensing coils may be arranged to surround one or more of the excitation coils.

The one or more of the plurality of pins may comprise one or more permanent magnetic materials. In such embodiments, the one or more pins may be the magnetic field generator.

The magnetic field generator may be an electromagnet or a permanent magnet.

A further magnetic field generator may be provided. The further magnetic field generator may be configured to generate a magnetic field to change the properties of one or more pins so as to suppress delamination. The further magnetic field generator may comprise one or more coils, an electromagnet and/or a permanent magnet.

The pins may comprise one or more ferromagnetic materials.

The composite component may be a fan blade or a casing of a gas turbine engine.

In a second aspect there is provided a gas turbine engine comprising the composite component according to the first aspect.

In a third aspect there is provided a composite component assembly comprising the composite component according to the first aspect.

The composite component assembly may comprise a control system. The control system may comprise a signal processing arrangement and control unit for detecting changes in magnetic flux from the signal received from the sensor.

The composite component assembly may comprise an output for outputting a signal indicative of whether or not delamination has occurred. The output may be a display unit.

The control unit may be configured to cause a magnetic field to be generated by the magnetic field generator, a further magnetic field generator, or the sensing coil, in the event that delamination or increased delamination is detected.

The control system may be a closed loop control system.

In a third aspect there is provided a method of detecting delamination of a composite component having a plurality of plies, and a plurality of pins extending transversely to the plies. The pins comprise a magnetic material. The method may comprise generating a magnetic field in a thickness direction of the plies and in a region of one or more of the pins; and in the event of delamination, detecting a change in magnetic flux resulting from the delamination.

In a fourth aspect there is provided a method of suppressing delamination of a composite component having a plurality of plies, and a plurality of pins extending transversely to the plies. The pins comprise one or more ferromagnetic magnetic materials. The method comprises generating a magnetic field in a thickness direction of the plies and in a region of one or more of the pins so as to change the properties of the pins (e.g. the shape and/or dimensions of the pins).

In embodiments where the pins comprise a ferromagnetic material, delamination may be detected using the method of the third aspect, and delamination may be suppressed using the method of the fourth aspect.

The detection and suppression of delamination may operate in a closed loop. If delamination is detected, delamination may be be suppressed. Once delamination is suppressed by a desired extent, delamination may be monitored until further delamination or increased delamination is detected. Then the delamination may again be suppressed. The process may continue in a closed loop. The delamination detection method may determine whether to suppress delamination.

In a fifth aspect there is provided a method of manufacturing a composite component. The method comprises laying up a plurality of plies to form a laminate; and inserting a plurality of pins in to the laminate that extend transversely to the plies. The pins comprise a magnetic material. A magnetic field generator is provided and configured to generate a magnetic field through a thickness direction of the component. A sensor is provided for detecting a change in magnetic flux indicative of delamination of the plies.

It will be appreciated by the person skilled in the art that the plurality of pins may be inserted before or after providing the magnetic field generator and/or before or after providing a sensor. The sensor may be provided before or after the magnetic field generator has been provided.

The magnetic field generator and/or the sensor may be provided by one or more coils, and the method may comprise providing the coils on a surface of one or more plies of the component.

The coil may be provided by laying a metallic sheet (e.g. a copper sheet) on an outer surface of a component pre-curing, and removing portions of the sheet to form a coil post-curing. Alternatively the coils may be provided directly pre or post curing. For example, the coil may be provided by a method of additive layer manufacturing.

The skilled person will appreciate that except where mutually exclusive, a feature described in relation to any one of the above aspects may be applied mutatis mutandis to any other aspect. Furthermore except where mutually exclusive any feature described herein may be applied to any aspect and/or combined with any other feature described herein.

DESCRIPTION OF DRAWINGS

Embodiments will now be described, by way of example only, with reference to the accompanying drawings in which.

DETAILED DESCRIPTION

Figure 1:
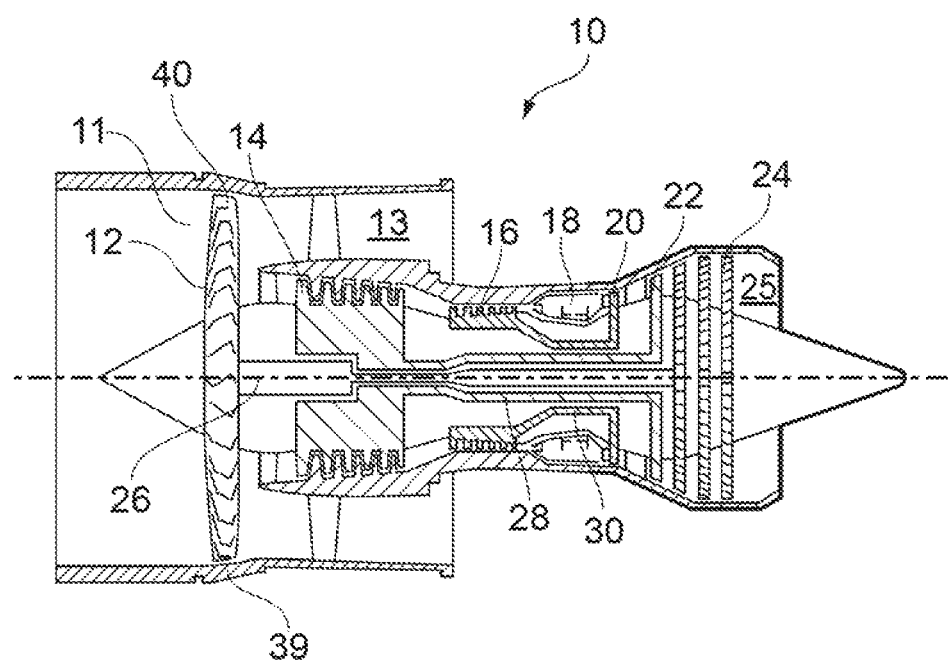
FIG. 1 is a sectional side view of a gas turbine engine.

With reference to FIG. 1 a bypass gas turbine engine is indicated at 10. The engine 10 comprises, in axial flow series, an air intake duct 11, fan 12, a bypass duct 13, an intermediate pressure compressor 14, a high pressure compressor 16, a combustor 18, a high pressure turbine 20, an intermediate pressure turbine 22, a low pressure turbine 24 and an exhaust nozzle 25. The fan 12, compressors 14, 16 and turbines 20, 22, 24 all rotate about the major axis of the gas turbine engine 10 and so define the axial direction of the gas turbine engine.

Air is drawn through the air intake duct 11 by the fan 12 where it is accelerated. A significant portion of the airflow is discharged through the bypass duct 13 generating a corresponding portion of the engine thrust. The remainder is drawn through the intermediate pressure compressor 14 into what is termed the core of the engine 10 where the air is compressed. A further stage of compression takes place in the high pressure compressor 16 before the air is mixed with fuel and burned in the combustor 18. The resulting hot working fluid is discharged through the high pressure turbine 20, the intermediate pressure turbine 22 and the low pressure turbine 24 in series where work is extracted from the working fluid. The work extracted drives the intake fan 12, the intermediate pressure compressor 14 and the high pressure compressor 16 via shafts 26, 28, 30. The working fluid, which has reduced in pressure and temperature, is then expelled through the exhaust nozzle 25 generating the remainder of the engine thrust.

The intake fan 12 comprises an array of radially extending fan blades 40 that are mounted to the shaft 26. The shaft 26 may be considered a hub at the position where the fan blades 40 are mounted. The fan blades are surrounded by a fan casing 39, which may be made from a composite material.

Figure 2:
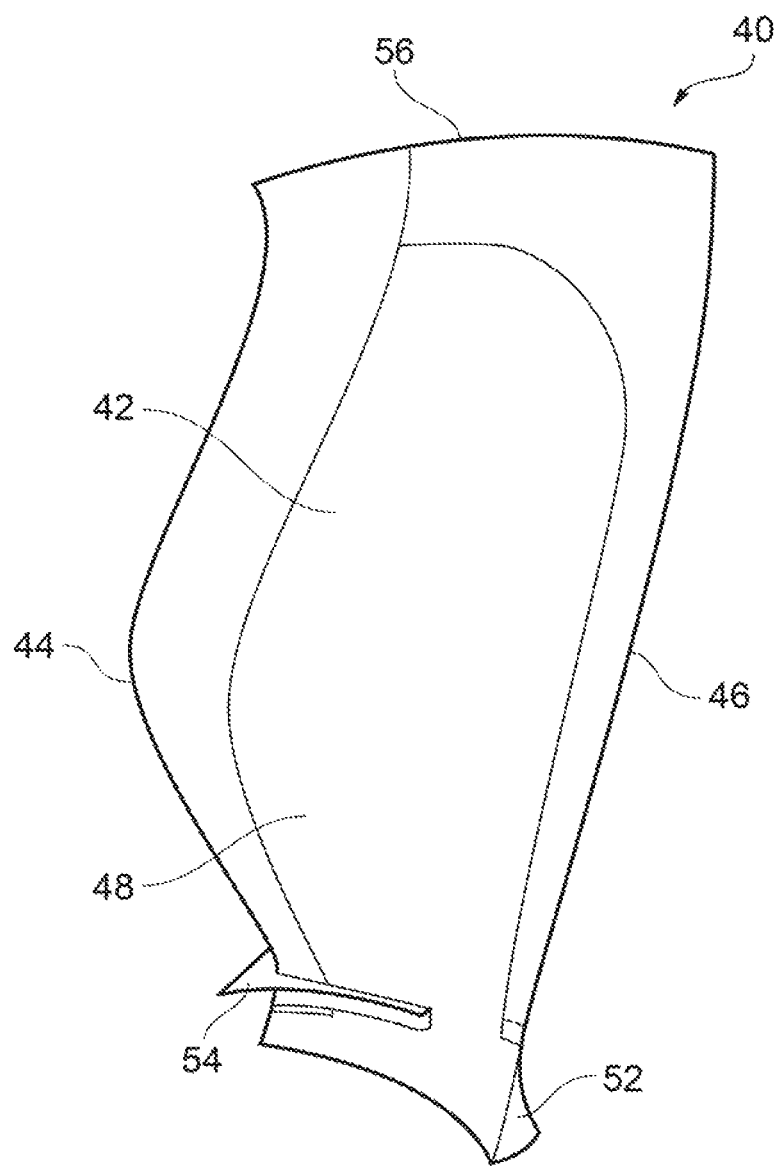
FIG. 2 illustrates a composite fan blade.

Referring to FIG. 2, the fan blades 40 each comprise an aerofoil portion 42 having a leading edge 44, a trailing edge 46, a concave pressure surface wall 48 extending from the leading edge to the trailing edge and a convex suction surface wall extending from the leading edge to the trailing edge. The fan blade has a root 52 via which the blade can be connected to the hub. The fan blade has a tip 56 at an opposing end to the root. The fan blade may also have an integral platform 54 which may be hollow or ribbed for out of plane bending stiffness. The fan blade includes a metallic leading edge and a metallic trailing edge. The remainder of the blade (e.g. the body of the blade) is made from composite material.

Figure 3:
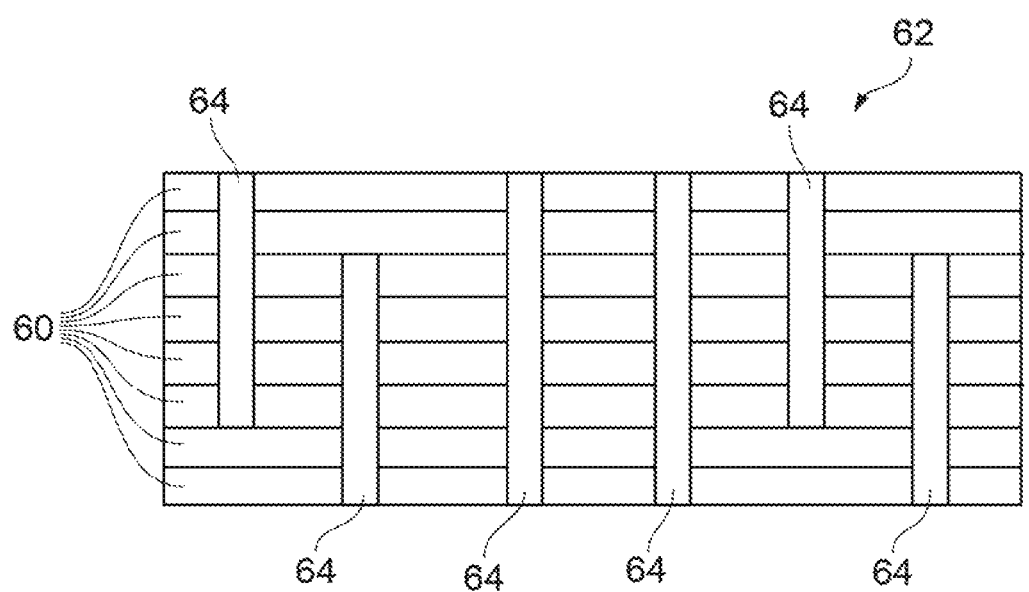
FIG. 3 illustrates a cross sectional view through a composite component.

Referring to FIG. 3, the composite material of the fan blade includes a plurality of plies 60 that together form a laminate 62. A plurality of pins 64 extend transversely to the plies. The pins may be arranged to extend through the full thickness of a component or through the partial thickness of a component, and/or a component may have pins extending from one surface of the component or from opposing surfaces of the component.

Figure 4:
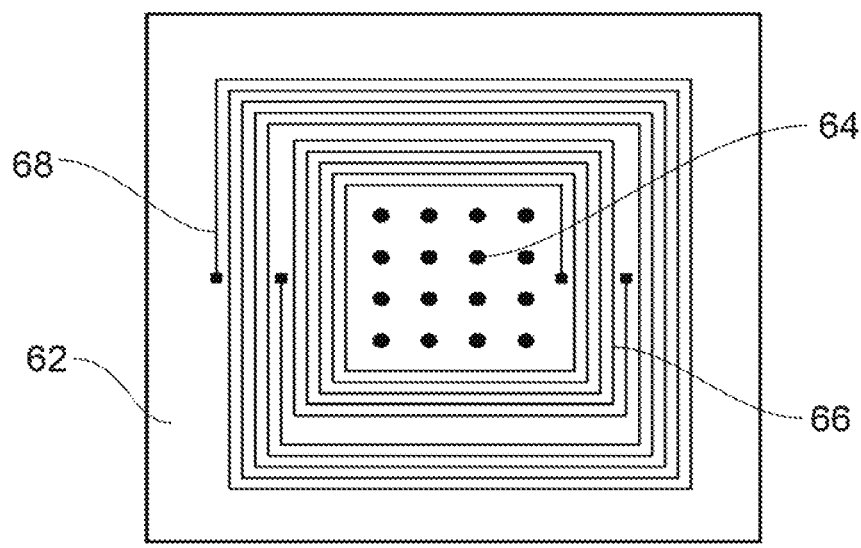
FIG. 4 illustrates a plan view of a composite component.

Referring now to FIG. 4, the pins 64 are made from a ferromagnetic material, for example a nickel-iron alloy, e.g. Ni80Fe20. In alternative embodiments the pins may be made from any suitable magnetic material. In the present example the pin array has a 2% areal density, but any suitable areal density may be selected.

In the present example, two coils 66, 68 are provided on the top and bottom surfaces of the laminate (that is on the exposed principle surface of the outer plies of the laminate). One of the coils 66 is used for sensing (i.e. is a type of sensor) and the other coil 68 is used for generating a magnetic field (i.e. is a type of magnetic field generator). As can be seen in FIG. 4, the sensing coil 66 surrounds a plurality of pins 64 that are in a region where delamination is to be monitored. The excitation coil 68 circumscribes the sensing coil 66. In the present example, the sensing coil and the excitation coil are made from copper, but in alternative embodiments any suitable conductive material, e.g. any suitable metal or metal alloy may be selected.

Figure 5:
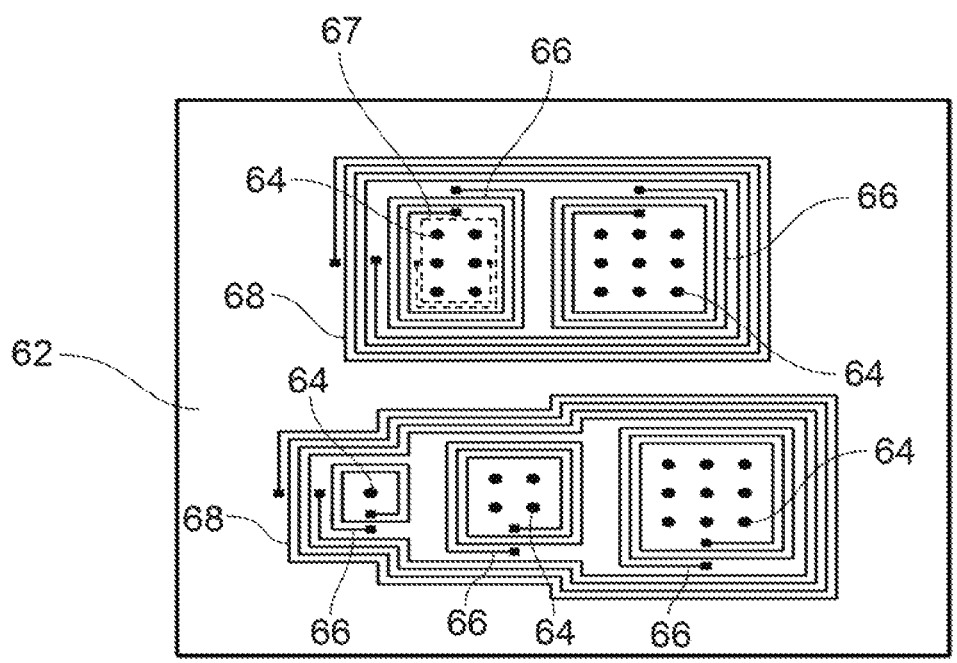
FIG. 5 illustrates a plan view of an alternative composite component.

An alternative arrangement of pins 64 and coils 66, 68 is shown in FIG. 5. In FIG. 5 there are multiple regions where delamination is being independently monitored. In this example a sensing coil is arranged around each of the one or more pins in the regions to be monitored. Unlike the previously described example, the excitation coils do not only circumscribe one sensing coil (and associated pins), instead they surround multiple sensing coils (and associated pins). Two excitation coils 68 are provided, one surrounds two of the sensing coils and the other surrounds three of the sensing coils, but it will be appreciated that any suitable number of sensing coils may be surrounded by each excitation coil.

In FIG. 5, the dotted coil 67 indicates a further magnetic field generator that may optionally be provided. The function of the further coil will be described later.

Figure 6:
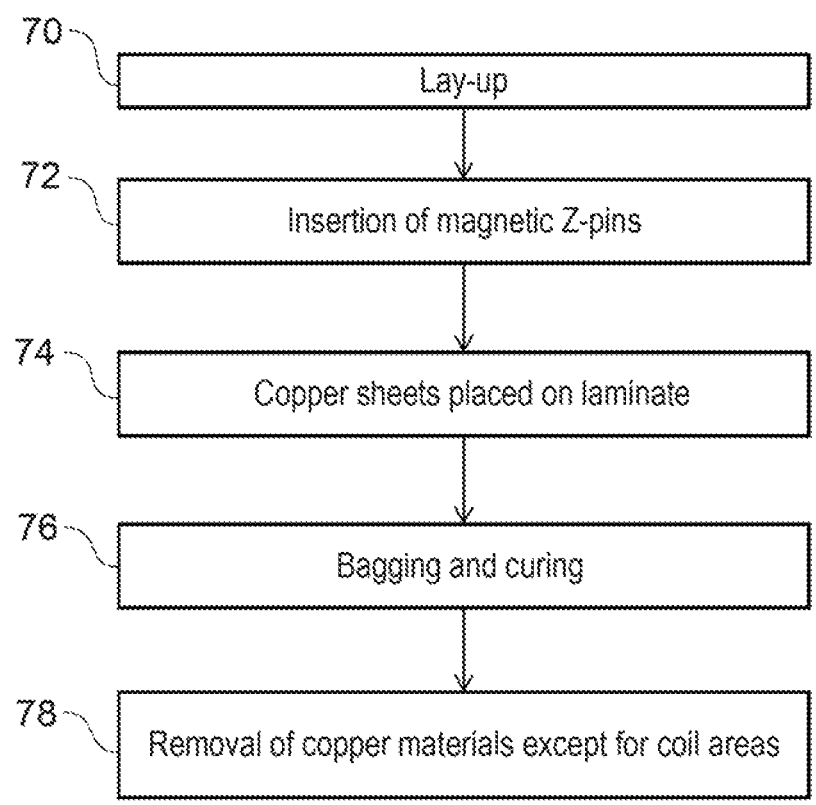
FIG. 6 is a block diagram of a method of manufacturing the composite component of FIG. 4 or 5.

Referring now to FIGS. 4, 5, and 6, to manufacture the composite component, firstly, as indicated at block 70, the plies are stacked one on top of the other (i.e. the plies are laid-up). This may be done manually or an automated process may be used (for example an automated fibre placement machine may be used).

Next, as indicated at block 72, the pins 64 are inserted into the stack of plies (now referred to as a laminate) in a direction that is transverse to the stack of plies. Then, as indicated at block 74, a copper sheet is placed on the top and bottom of the laminate (that is one copper sheet is placed on each of the exposed principal ply surfaces). The pins may be inserted using a method described in U.S. Pat. No. 8,893,367 which is incorporated herein by reference, or for example using an ultrasonic hammer.

The composite component is then usually bagged before being cured, indicated at block 76. Bagging and curing bonds the plies together to secure the plies within the laminate structure. Once cured the composite component is removed from the bag.

As indicated at step 78, the portions of the copper on the outer surface of the laminate are removed using a process such as chemical etching or laser etching, so as to form the coils 66 and 68 (and optionally coil 67).

In alternative methods, instead of applying a copper sheet to an outer surface of the composite component and then removing portions of the copper sheet, the coil pattern could be applied directly to the surface. For example, the coil may be printed on the surface, e.g. using additive layer manufacturing. Alternatively, wire or strips may be pre-formed or cut and positioned on the surface. In these embodiments, the coil may be laid on the surface of the laminate before or after curing.

Figure 7:
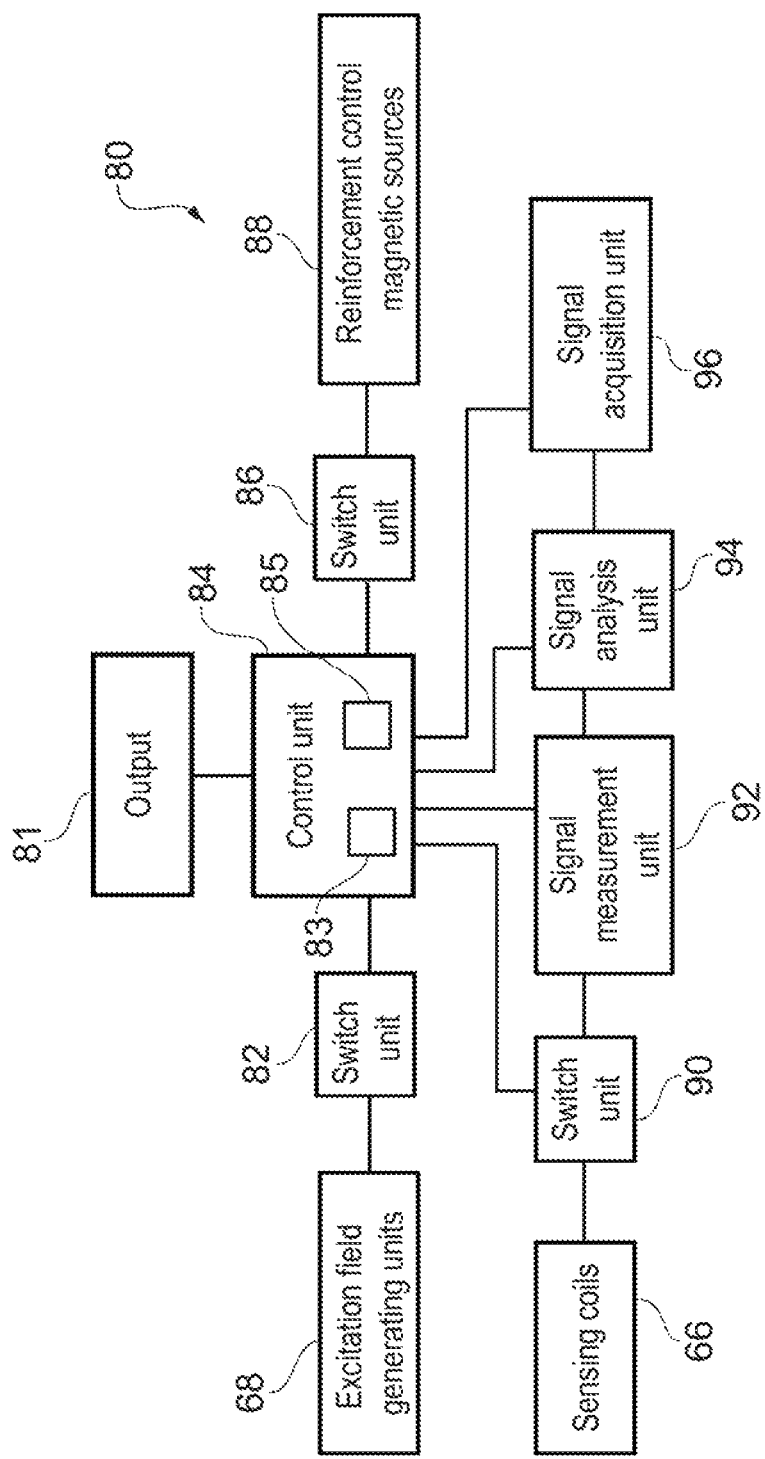
FIG. 7 illustrates a control system for use with the composite component of FIG. 4 or 5.

Referring now to FIG. 7, a control system for use with the described composite components is indicated generally at 80.

In the following description, the terms 'connected' and 'coupled' mean operationally connected and coupled. It should be appreciated that there may be any number of intervening components between the mentioned features, including no intervening components.

The control system 80 includes a control unit 84. The control unit 84 may comprise any suitable circuitry to cause performance of the methods described herein. The control unit 84 may comprise: at least one application specific integrated circuit (ASIC); and/or at least one field programmable gate array (FPGA); and/or single or multi-processor architectures; and/or sequential (Von Neumann)/parallel architectures; and/or at least one programmable logic controllers (PLCs); and/or at least one microprocessor; and/or at least one microcontroller, to perform the methods.

By way of an example, the control unit 84 may comprise at least one processor 83 and at least one memory 85. The memory 85 may store a computer program comprising computer readable instructions that, when read by the processor 83, causes performance of the methods described herein. The computer program may be software or firmware, or may be a combination of software and firmware.

The processor 83 may be located on the gas turbine engine 10, or may be located remote from the gas turbine engine 10, or may be distributed between the gas turbine engine 10 and a location remote from the gas turbine engine 10. The processor 83 may include at least one microprocessor and may comprise a single core processor, or may comprise multiple processor cores (such as a dual core processor or a quad core processor).

The memory 85 may be located on the gas turbine engine 10, or may be located remote from the gas turbine engine 10, or may be distributed between the gas turbine engine 10 and a location remote from the gas turbine engine 10. The memory 85 may be any suitable non-transitory computer readable storage medium, data storage device or devices, and may comprise a hard disk and/or solid state memory (such as flash memory). The memory 85 may be permanent non-removable memory, or may be removable memory (such as a universal serial bus (USB) flash drive).

An output 81, for example a visual display, may be connected to the control unit and configured to display information outputted from the control unit.

The sensing coils are connected to a signal measurement unit 92 via a switching unit 90. The switching unit is provided so that if there are more than one sensing coils the output from each sensing coil can be selectively sent to the signal measurement unit 92. The measured signals are sent to a signal analysis unit 94 and a signal acquisition unit 96, for processing. Each of the switch unit 90, the signal measurement unit 92, the signal analysis unit 94, and the signal acquisition unit 96 are also connected to and controlled by the control unit 84.

A switch unit 82 is also arranged with the excitation coils 68. When there are a plurality of excitation coils, the switching unit 82 can be used to selectively permit current to be directed to one or more of the excitation coils, under the control of the control unit 84.

A further switch unit 86 is arranged with a reinforcement control magnetic sources 88, in order to selectively activate one or more magnetic sources under the control of the control unit 84. The magnetic source 88 may be one or more of the sensing coils 66, one or more of the excitation coils, or when a further coil 67 is provided the further coil.

Figure 8:
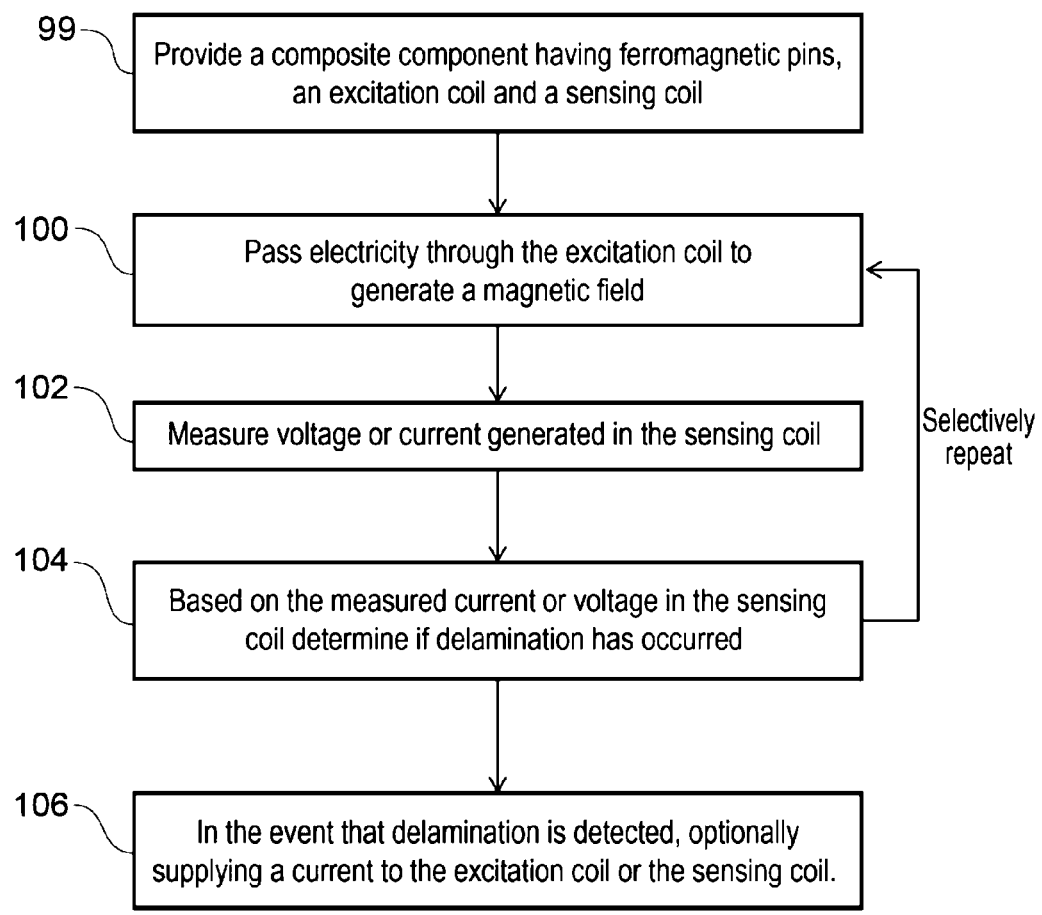
FIG. 8 is a block diagram of a method of detecting delamination and optionally suppressing delamination.

A method of detecting delamination and optionally suppressing delamination will now be described with reference to FIG. 8. As indicated in block 99, a composite component, such as the ones previously described, is provided. In this example the composite component includes ferromagnetic pins 64, excitation coils 68 and sensing coils 66. The excitation coils 68 and the sensing coils 66 are connected to the control system 80. The coils and/or sensing coils may be connected directly or remotely.

At block 100, electricity is passed through the excitation coil 68 so as to generate a magnetic field, which the skilled person will understand to be explained using Maxwell's equations. If there are multiple excitation coils 68, the switch unit 82 (controlled by the control unit 84) determines to which excitation coil electricity is supplied.

At block 102, the voltage or current generated in the sensing coil is measured. If there are multiple sensing coils, the switch unit 90 (controlled by the control unit) determines which sensing coil should be measured.

At block 104, based on the measured current or voltage in the sensing coil a determination is made as to whether delamination has occurred. The signal processing arrangement (e.g. the voltage measurement unit, signal analysis unit and the signal acquisition unit) sends information to the control unit about the measured current or voltage. The control unit then determines whether delamination has occurred. The method of blocks 100, 102 and 104 may be selectively repeated. The repeat interval may be determined by whether or not delamination has been detected and/or the extent of delamination. As described later, in embodiments where delamination is optionally suppressed the repeat interval may be determined by the amount of suppression. Alternatively, the process may be repeated at a fixed interval, or may operate on a continuous loop.

During delamination (and/or at the onset of delamination) one or more of the pins in the area of delamination will start to move (i.e. pull-out) and/or deform. This movement and/or deformation will cause a change in the magnetic flux passing through the sensing coil 66 and induce voltage or current output from the sensing coil, according to Maxwell's equations.

If there is no deformation or movement there will be no change in magnetic flux, and as such no current or voltage will be output from the sensing coil 66, which will indicate that there is no delamination.

If delamination is in progress, there will be a change in the magnetic flux and as such a current or voltage will be output. The magnitude of the current or the voltage will be indicative of the loading rate, i.e. the deformation or movement rate of the pins; that is the greater the current or voltage the greater the loading rate, and therefore the greater the likely extent of delamination.

Once delamination has been detected this can be output via output 81, e.g. via a display.

In some examples, if the control unit 84 detects that delamination has occurred the system may be configured to suppress the delamination (e.g. if it is below a certain extremity). In such an example, as indicated at block 106, electricity may be directed to the excitation coil 68 or the sensing coil 66. In doing this, an increased or an additional magnetic field is induced. The pins are made from a ferromagnetic material and such materials exhibit magnetostrictive properties. This means that the increased or additional magnetic field can be used to change the shape of the pin, e.g. increase the diameter of the pin. In doing so, the friction between the laminate and the pin(s) 64 is increased, which can suppress delamination.

Referring back to FIG. 7, delamination can be suppressed in this way via the control unit 84 causing electricity to be passed through one or more reinforcement control magnetic sources 88, which in this example may be the excitation coil 68 or the sampling coil 66. In alternative embodiments an additional magnetic field generator, e.g. coil 67, may be provided and this additional magnetic field generator may be used to suppress delamination.

Figure 9:
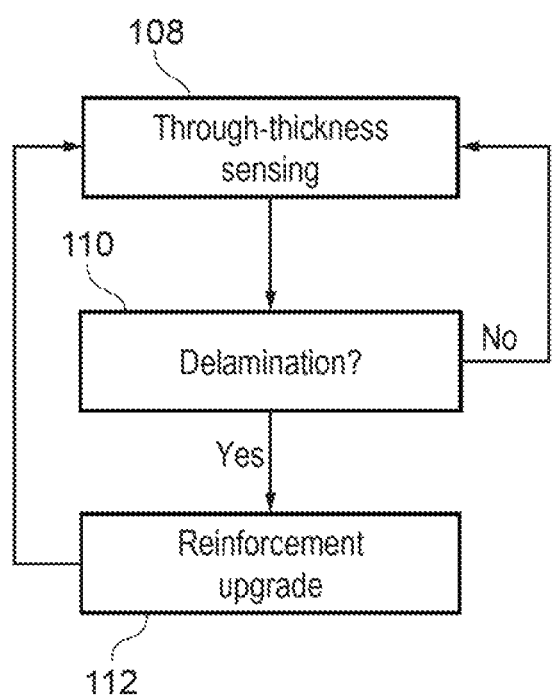
FIG. 9 is a block diagram of a closed loop that can be used in the method of FIG. 8 or an algorithm stored in a memory of the control system of FIG. 7.

Referring now to FIG. 9, the control system shown in FIG. 7 can be arranged to operate in a closed loop. At block 108, the system is used to detect delamination. At block 110, a determination detection step is made. If no delamination or no increase in delamination is detected then the sensing process continues until delamination or an increase in delamination is detected. If delamination has occurred or deteriorated, the control system will induce a magnetic field to restrict the delamination (indicated at block 112). Once the restriction to delamination has been achieved and/or increased, the system continues to monitor delamination.

Advantageously, the composite component described and/or the method described can be used to detect delamination in a composite component. Detection of delamination can contribute to effective life management of a component.

Further, the pins and the system can be configured and arranged such that delamination can be suppressed, furthering the life of a composite component.

The arrangement of the coils is such that the properties of the pins can be sensed without contacting the pins. This can ease manufacture and also means that any noise caused by contacts with the pins can be prevented.

The magnetic field generator has been described above as being a coil, but in alternative examples the generator may be an electromagnet or a permanent magnet. In further alternative embodiments the pin may be made partly or fully from a permanent magnet, and in such embodiments the pin may act as a magnetic field generator.

In the described examples, the excitation coils, the sensing coils, and/or the additional coil 67 are used to generate a magnetic field to suppress delamination, but in alternative embodiments delamination may be suppressed by one or more electromagnets or one or more permanent magnets. In the case of permanent magnets, the permanent magnets may be added to the composite component once delamination is detected.

The pins may be made from a single material or the pin may be a hybrid pin which may include magnetic and non-magnetic materials. For example, the pin may include one or more magnetic materials and one or more non-magnetic materials.

In the described examples, the coils are provided on the outer surfaces of the composite component, but in alternative embodiments, the coils may be provided on one or more inner plies of the component.

In further alternative embodiments, an electromagnetic interference shield may be provided to reduce magnetic interference between components of the system.

In yet further alternatives, a protective coating may be provided on the outer surface of the composite component.

It will be understood by the person skilled in the art that the described examples relate a fan blade, but in alternative examples the composite component may be a casing for a gas turbine engine. In further alternative embodiments, the composite component may be any other composite component.

It will be understood that the invention is not limited to the embodiments above-described and various modifications and improvements can be made without departing from the concepts described herein. Except where mutually exclusive, any of the features may be employed separately or in combination with any other features and the disclosure extends to and includes all combinations and sub-combinations of one or more features described herein.

The invention claimed is:

1. A composite component assembly comprising a composite component having:
   a plurality of plies;
   a plurality of pins extending transversely to the plies, wherein the pins comprise a magnetic material;
   a magnetic field generator configured to generate a magnetic field through a thickness direction of the component; and
   a sensor for detecting a change in magnetic flux indicative of delamination of the plies, the sensor being an electrically conductive coil provided around one or more of the plurality of pins, and the coil being provided on a surface of one or more of the plurality of plies.

2. The composite component assembly according to claim 1, wherein the composite component comprises a sensor in regions where prevention of delamination is critical and no sensors are provided in regions where delamination is acceptable.

3. The composite component assembly according to claim 1, wherein the composite component comprises a sensor in regions where prevention of delamination is critical and no sensors are provided in regions where delamination is acceptable.

4. The composite component assembly according to claim 1, wherein the magnetic field generator is an electrically conductive coil.

5. The composite component assembly according to claim 1, wherein the one or more of the plurality of pins are made from one or more permanent magnetic materials and the one or more pins are the magnetic field generator.

6. The composite component assembly according to claim 1, wherein the pins comprise one or more ferromagnetic materials.

7. The composite component assembly according to claim 1, wherein the composite component is a fan blade or a casing of a gas turbine engine.

8. A gas turbine engine comprising the composite component according to claim 1.

9. The composite component assembly according to claim 1, further comprising
   a control system including a signal processing arrangement and processor programmed to detect changes in magnetic flux from the signal received from the sensor.

10. The composite component assembly according to claim 9, comprising an output and outputting a signal indicative of whether or not delamination has occurred.

11. The composite component assembly according to claim 10, wherein the output is a display unit.

12. The composite component assembly according to claim 10, wherein the processor is configured to cause a magnetic field to be generated by the magnetic field generator, a further magnetic field generator, or the sensing coil, in the event that delamination or increased delamination is detected.

13. The composite component assembly according to claim 9, wherein the control system is a closed loop control system.

14. A method of detecting delamination of a composite component having a plurality of plies, and a plurality of pins extending transversely to the plies, wherein the pins comprise a magnetic material, the method comprising:
   generating a magnetic field in a thickness direction of the plies and in a region of one or more of the pins; and
   in the event of delamination, detecting a change in magnetic flux resulting from the delamination via a sensor, the sensor being an electrically conductive coil provided around one or more of the plurality of pins, and the coil being provided on a surface of one or more of the plurality of plies.

15. The method according to claim 14, wherein the pins comprise one or more ferromagnetic materials.

16. The method according to claim 15, further comprising, in the event of delamination, generating a magnetic field in a thickness direction of the plies and in a region of one or more of the pins so as to change the properties of the pins and supress delamination of the composite component.

17. The method according to claim 16, wherein detection and suppression of delamination operates in a closed loop.

18. A method of manufacturing a composite component comprising:
   laying up a plurality of plies to form a laminate;
   inserting a plurality of pins to the laminate that extending transversely to the plies, the pins including a magnetic material;
   providing a magnetic field generator configured to generate a magnetic field through a thickness direction of the component; and
   providing a sensor for detecting a change in magnetic flux indicative of delamination of the plies, the sensor being an electrically conductive coil provided around one or more of the plurality of pins, and the coil being provided on a surface of one or more of the plurality of plies.

* * * * *